United States Patent [19]
Breznak et al.

[11] Patent Number: 5,589,352
[45] Date of Patent: Dec. 31, 1996

[54] DIFFUSION GRADIENT CHAMBER SYSTEM

[75] Inventors: John A. Breznak; David Emerson, both of East Lansing; John K. Koh, Ann Arbor, all of Mich.

[73] Assignees: Board of Trustees operating Michigan State University, East Lansing; Koh Development, Inc., Ann Arbor, both of Mich.

[21] Appl. No.: 466,758

[22] Filed: Jun. 6, 1995

Related U.S. Application Data

[63] Continuation of Ser. No. 117,222, Sep. 3, 1993.

[51] Int. Cl.[6] ............................. C12Q 1/02; C12Q 1/04; C12M 3/00; C12M 1/00
[52] U.S. Cl. ................ 435/34; 435/29; 435/287.1; 435/808; 435/809; 435/288.7; 435/297.2
[58] Field of Search ...................... 435/29, 34, 284, 435/287, 310, 301, 808, 809

[56] References Cited

PUBLICATIONS

Lawrence, et al. Journal of Bacteriology vol. 174 No. 17 pp. 5732–5739 (1992).
Emerson et al. ASM Intl Conf. on Multicellular Behavior of Bacteria Oct. 21–25 1990, Woods Hole, MA.
Wolfaardt et al., Applied and Environmental Microbiology 59 2388–2396 (1993).
Emerson, D., and Breznak, J. A., Wood's Hole, American Society of Microbiology (Oct. 21–25, 1990).
J. A. Breznak, Emerson, D., Worden, M., and Oriel, P., International Society for Microbial Ecology, Sep. 10, 1992.
Wolfe, A. J., and H. C. Berg, Proc. Natl. Acad. Sci. USA 86:6973–6977 (1989).
Macnab, R. M., Motility and chemotaxis in: *Escherichia coli* and *Salmonella typhimurium* (F. C. Neihardt et al eds) ASM (1987)).

Bourret, et al., Annu. Rev. Biochem. 60:401–441 (1991).
Caldwell, D. E., et al., Can. J. Microbiol. 19, 53–58 (1973).
Caldwell, D. E., et al., Bull. Ecol. Res. Comm. (Stockholm) 17:151–158 (1973).
Wimpenny, J. W. T., et al., One–Dimensional Gel–Stabilized Model Systems. CRC Handbook of Laboratory Model Systems for Microbial Ecosystems, vol. II CRC Press, Boca Raton (1988).
Wimpenny, J. W. T., et al., Gel–Plate Methods in Microbiology. CRC Handbook of Lab. Model Sys. for Microbial Ecosystems., vol. I (Wimpenny, J. W. T., ed.) CRC Press, Boca Raton (1988).
Thomas. L. V., and Wimpenny, J. W. T., Applied and Environmental Microbiology, pp. 1991–1997 (Jun. 1993).
Nelson, D. C., et al., Applied and Environmental Microbiology, pp. 161–168 (Jul. 1986).
Wolfaardt, G. M., et al., Applied and Environmental Microbiology, pp. 2388–2396 (Aug. 1993).
Hannoun and Stephanopolous, Biotechnology and Bioengineering vol. SSVII, 829–836 (1986).
Kelly, et al., Bacterial Chemotaxis and Microbial Competition 16, 115–131 (1988).

*Primary Examiner*—Donald E. Czaja
*Assistant Examiner*—Jane Williams Elkin
*Attorney, Agent, or Firm*—Ian C. McLeod

[57] ABSTRACT

A system (10) and method of use for observation of microorganisms in a controlled environment is described. The system uses a diffusion gradient chamber (12) with reservoirs (24) which provide a compound or analyte (S) through a membrane (20) into a space in the chamber containing the microorganisms. The system preferably uses a camera (40) which records the observations of the microorganisms. The system enables study of microorganisms in gradients of compounds and the isolation of useful microorganisms.

34 Claims, 11 Drawing Sheets

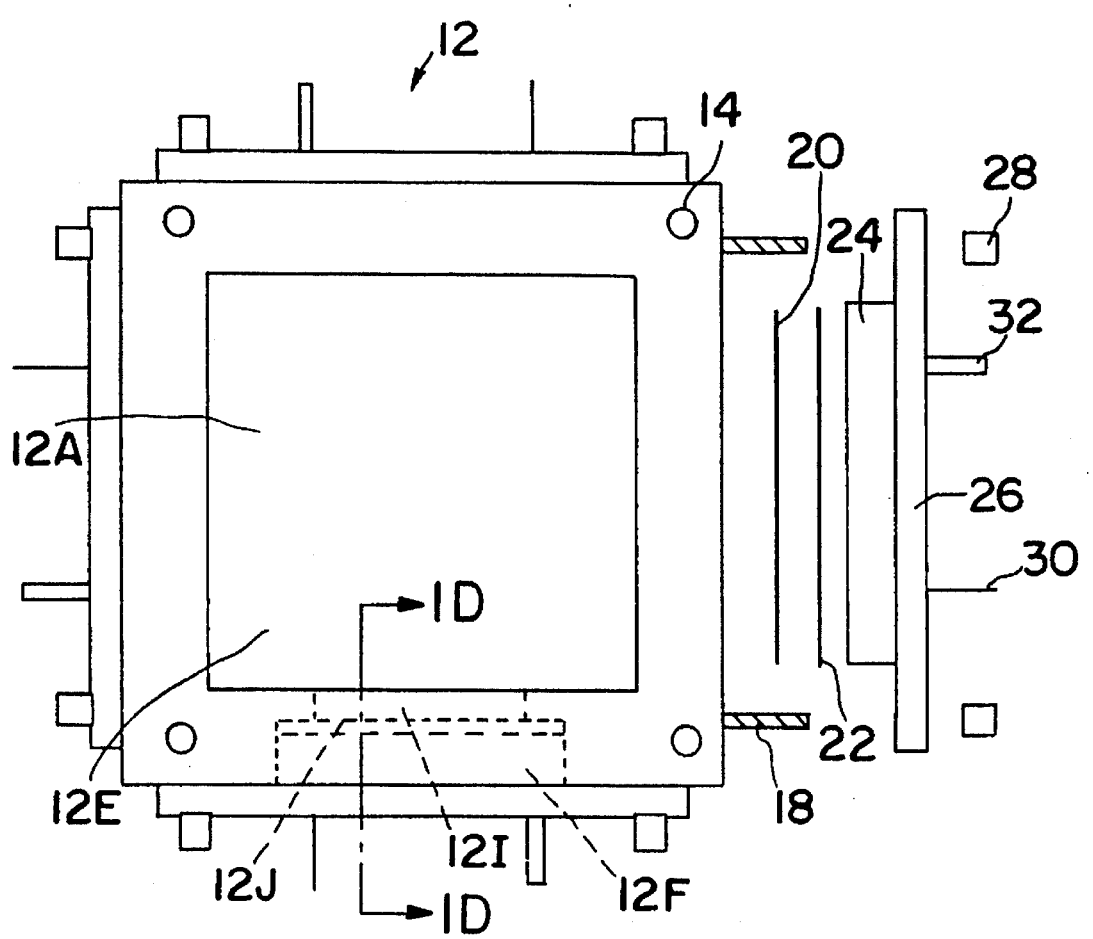
FIG. IA
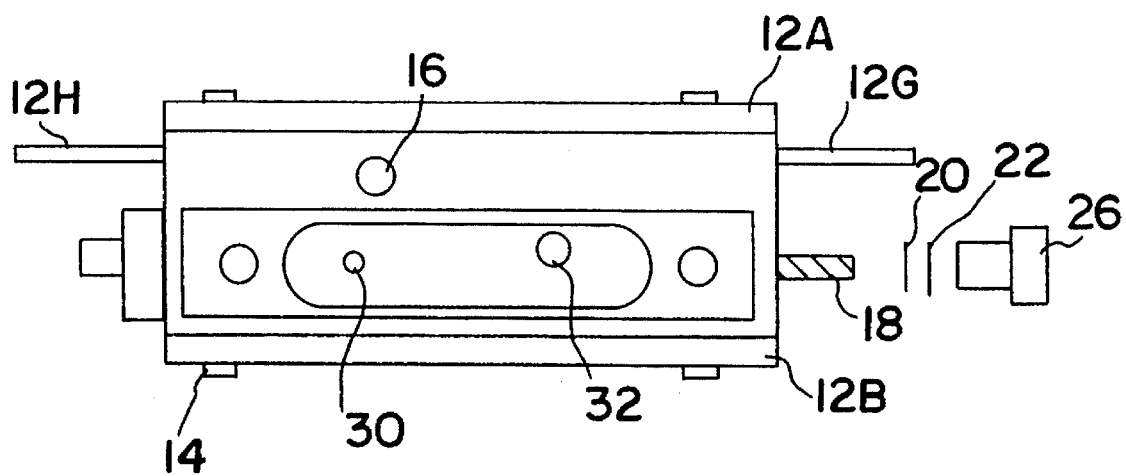
FIG. IB

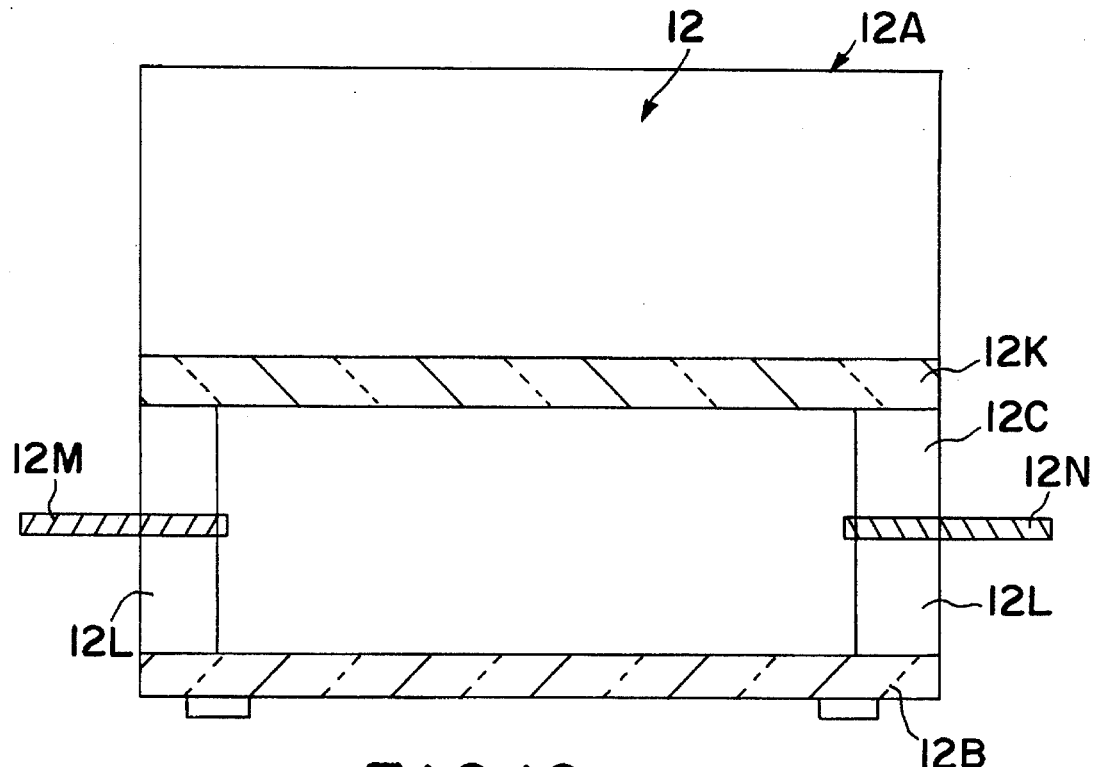
FIG.IC
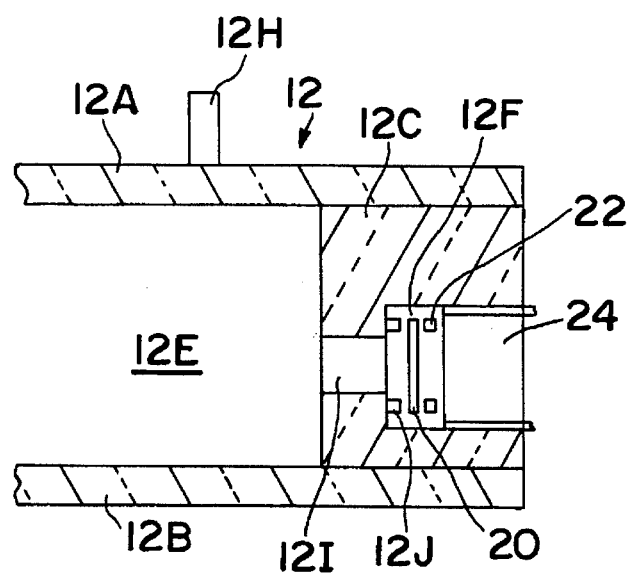
FIG.ID

ASPARTATE    SERINE
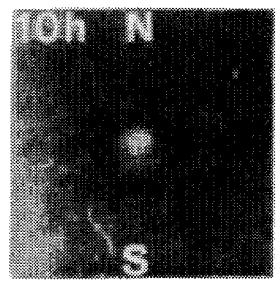
FIG.9A
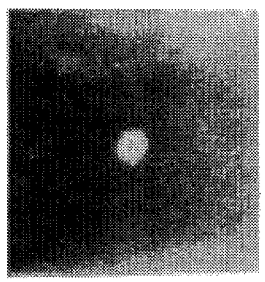
FIG.9E
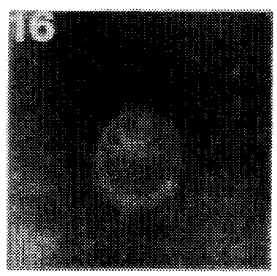
FIG.9B
FIG.9F
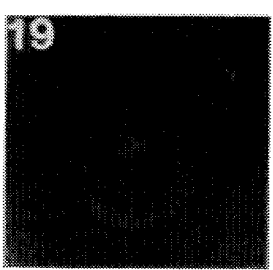
FIG.9C
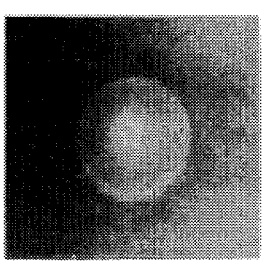
FIG.9G
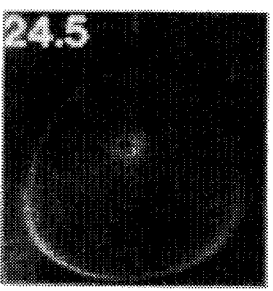
FIG.9D
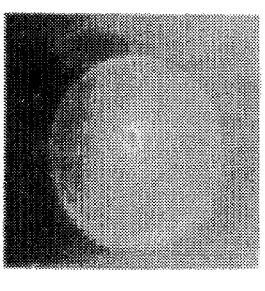
FIG.9H Che−　　　　Che−　　　　Mot−

↑
0.1 mM
ASPARTATE

|  E. coli | E. coli – P. fluorescens | P. fluorescens |
|---|---|---|
| 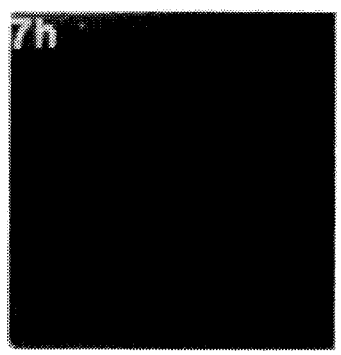 | 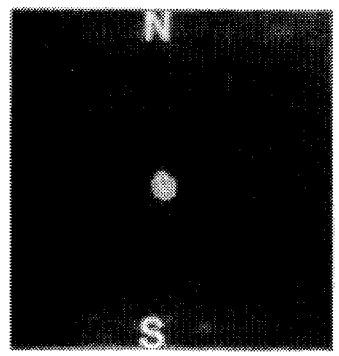 | 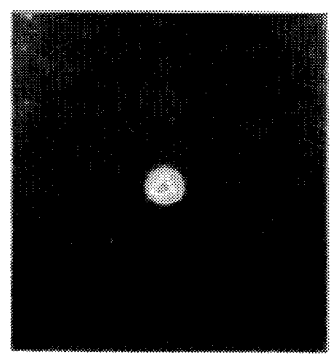 |
| FIG.IIA | FIG.IID | FIG.IIG |
| 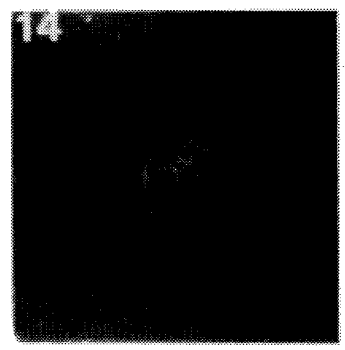 | 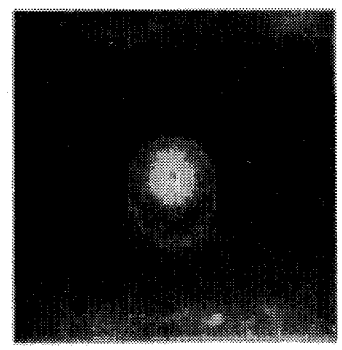 | 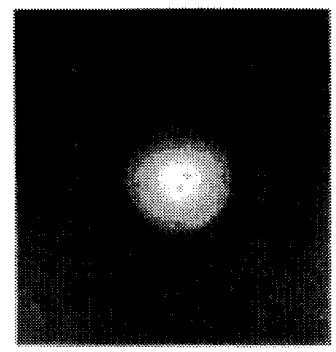 |
| FIG.IIB | FIG.IIE | FIG.IIH |
| 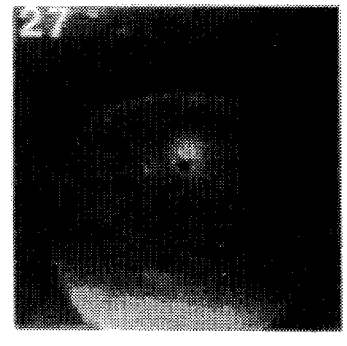 | 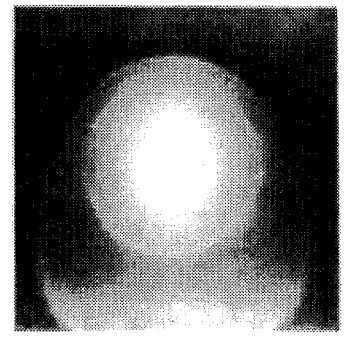 | 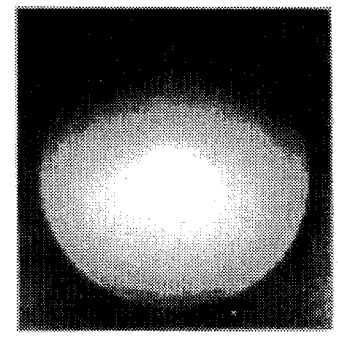 |
| FIG.IIC | FIG.IIF | FIG.III |

DIFFUSION GRADIENT CHAMBER SYSTEM

This is a continuation of copending application Ser. No. 08/117,222 filed on Sep. 3, 1993.

BACKGROUND OF THE INVENTION

(1) Field of the Invention

The present invention relates to a diffusion gradient chamber system for determining the affects of various environments on microorganisms. In particular the present invention relates to a system which enables recording of the results of tests in dynamically changing environments.

(2) Description of Related Art

Microbial life in nature exists in gradients of light intensity, temperature, pH, viscosity, oxygen and other soluble nutrients. Microbes have evolved mechanisms to position themselves in regions of such gradients that favor their growth and/or survival. Numerous examples exist of these phenomena. For example, the chemoautotrophic sulfide oxidizing bacterium Beggiatoa can respond rapidly to vertical gradients of oxygen, light, and sulfide. This response allows it to position itself optimally in a microaerobicniche where it can oxidize sulfide diffusing up from anoxic zones. The chemotactic response itself has been studied extensively in *Escherichia coli*. It is well understood that *E.coli* cells move in a random walk consisting of runs and tumbles and that *E.coli* is capable of biasing its random walk by increasing its run time when swimming up a gradient of a chemoattractant or down a gradient of a repellent, the end result is more rapid migration toward an attractant or away from a repellent. The sharply defined "blooms" of purple and green sulfur bacteria in the thermocline region of stratified lakes are a well known example of such positioning and reflect the presence of chemo- and photosensory, locomotory, and buoyancy mechanisms in the cells.

Most systems employed for isolation, cultivation and study of microbes in the laboratory are homogeneous and do not sufficiently imitate the dynamic and diffusive character of natural habitats. Consequently, there is only limited understanding of the behavior of microbes confronted with multiple gradients of environmental cues. Indeed, it may well be that natural habitats hold a variety of organisms capable of growth only within a very narrow range of environmental conditions. Such "stenobiotic" organisms might constitute much of the untapped diversity believed to exist in nature and represent organisms that have eluded isolation with conventional, homogeneous culture systems. In addition, it is possible that the physiological responses of organisms growing in gradients of nutrients may differ from those growing in homogeneous culture.

One approach to mimicking the spatial and temporal heterogeneity of natural habitats is to use gel-stabilized media within which defined diffusion gradients may be imposed. Pioneers of this approach include Caldwell and Wimpenny (Caldwell, D. E. and Hirsch, P., Can. J. Microbiol. 19, 53–58 (1973); Caldwell, D. E., Lai, S. H., and Tiedje, J. M., Bull. Ecol. Res. Comm. (Stockholm) 17:151–158 (1973); Wimpenny, J. W. T. and Errol Jones, One-Dimensional Gel-Stabilized Model Systems. CRC Handbook of Laboratory Model Systems for Microbial Ecosystems., Vol II (Wimpenny, J. W. T., ed.) CRC Press, Boca Raton (1988); Wimpenny, J. W. T., P. Waters and A. Peters, Gel-Plate Methods in Microbiology. CRC Handbook of Laboratory Model Systems for Microbial Ecosystems., Vol. I (Wimpenny, J. W. T., ed.) CRC Press, Boca Raton (1988); and Thomas, L. V., and Wimpenny, J. W. T., Applied and Environmental Microbiology, p. 1991–1997 (June 1993)) and others who created 1- and 2-dimensional gradients and used these to study the growth and behavior of pure cultures of bacteria, as well as of microbial communities in situ in lake sediments. More recently, Nelson (Nelson, D. C., Revsbech, N. P., and Jorgensen, B. B., Applied and Environmental Microbiology, p. 161–168 (July 1986)) and co-workers characterized the microscale growth of Beggiatoa at the interface of opposing $O_2$ and HS gradients in semisolid medium, and they also verified the ability of this bacterium to grow chemolithoautotrophically. See also Wolfaardt, G. M., et al., Applied and Environmental Microbiology, p. 2388–2396 (Aug. 1993).

The system of the present invention uses a diffusion gradient chamber in the form of a box with four (4) sides which allows up to four (4) variables to be studied by introducing them into a gel medium and studying the result of the gradients as described in an Abstract by Emerson, D. and Breznak, J. A., (Wood's Hole, American Society of Microbiology (Oct. 21–25, 1990)). A similar presentation appears in an Abstract by J. A. Breznak, Emerson, D., Worden, M., and Oriel, J. P., International Symposium on Microbial Ecology, Sep. 10, 1992. The system described was not capable of recording the results.

The problem is that it is difficult to visualize the microorganisms growing on the media and even more difficult to produce pictures of the microorganisms. There are also problems with the materials of construction which affect the results in use of the chamber.

OBJECTS

It is therefore an object of the present invention to provide a simple, yet analytical, diffusion gradient chamber system capable of achieving and recording steady state and long term continuous gradients of small soluble molecules and/or gases (1) for enrichment and isolation of potentially novel microorganisms (2) and for studies of the behavior of pure and mixed cultures of microbes in the presence of multiple gradients of environmental parameters. Further, it is an object of the present invention to provide a system which creates and records multiple, well characterized chemical diffusion gradients that mimic those found in natural ecosystems. Still further, it is an object of the present invention to provide a system which is well integrated such that its basic operation is able to be learned quickly and such that an experiment is able to be set up within eight (8) hours. Further, it is an object of the present invention to provide a system for enrichment and isolation of potentially novel organisms (e.g. stenobiotic bacteria, microaerophiles, detoxifying denitrifiers and anaerobes). Still further, it is an object of the present invention to provide a system for evaluating synergistic interactions between different microbes or synergistic effects of different solutions (e.g. antimicrobial agents) on a single microbe. Further, it is an object of the present invention to provide a system which, when coupled with microsensors and molecular genetic techniques, can be used as a tool for studying the environmental regulation of gene expression in axenic or defined mixed cultures. It is an object of the present invention to provide a system which can serve as an educational tool to illustrate microbial positioning mechanisms. Further, the present invention provides a diffusion gradient chamber system which allows for producing a permanent record of the growth of the microorganisms. Finally the present invention provides a diffusion gradient chamber system which is relatively simple and economical to construct. These and other objects will become increasingly apparent from the following description and the drawings.

BRIEF DESCRIPTION OF THE DRAWINGS

FIG. 1A is a top view of the diffusion gradient chamber 12 of the present invention showing a central arena 12E defining a window in top plate 12A attached by screws 14, well 12F for a reservoir 24 with an external face plate 26, a semi-permeable membrane 20 and a surrounding gasket 22.

FIG. 1B is a right side view of the gradient diffusion chamber 12 showing the top plate 12A and a bottom plate 12B defining a window similar to the top plate 12A and attached by screws 14, a filler port 16 for the chamber 12, and an inlet tube 30 and an outlet tube 32 for the reservoir 24.

FIG. 1C shows an embodiment for supplying a gas to the chamber 12 through a porous wall 12K.

FIG. 1D is a partial cross-sectional view of FIG. 1 along the line 1D—1D showing the well 12F with the lip 12, the gasket 22, the membrane 20 and the reservoir 24.

FIGS. 9A to 9H are photographs showing a comparison of the chemotactic response of E. coli HCB 33 to gradients of aspartate and serine in the system of FIG. 3. Two gradient chambers 12 were set up in parallel, one receiving 0.1 mM aspartate and the other 0.1 mM serine, both from the S reservoir 24. The N, E, and W reservoirs 24 were as described in the legend to FIG. 6. The chambers 12 were inoculated in the center with E. coli cells 13 h after the gradient was initiated. Note that the migration of E. coli toward the aspartate gradient (FIGS. 9A to 9D) has begun within 10 h of inoculation while a strong bias toward serine is not evident until around 16 h (FIGS. 9E to 9H). The direction of bias toward serine is perpendicular to the gradient, while toward aspartate there is also a tangential bias.

FIGS. 11A to 11I are photographs showing the separation of E. coli HCB 33 and P. fluorescens in a gradient of aspartate and valine. Three parallel chambers 12 were set up in the system of FIG. 3. The aspartate source, 0.1 mM, was on the N side of reservoir 4, and the valine source, 0.25 mM, was on the S side of reservoir 24, the E and W reservoirs 24 were sealed off. All three chambers 12 were inoculated 18 hours after the gradients were initiated. The chamber 12 in the left panel was inoculated with E. coli only; the chamber in the right panel was inoculated with P. fluorescens only and the chamber 12 in the middle with a 1:1 mixture of the 2 organisms. At 27 h the mixed chamber was sampled for the bacteria.

DETAILED DESCRIPTION OF THE PREFERRED EMBODIMENTS

Figure 2:
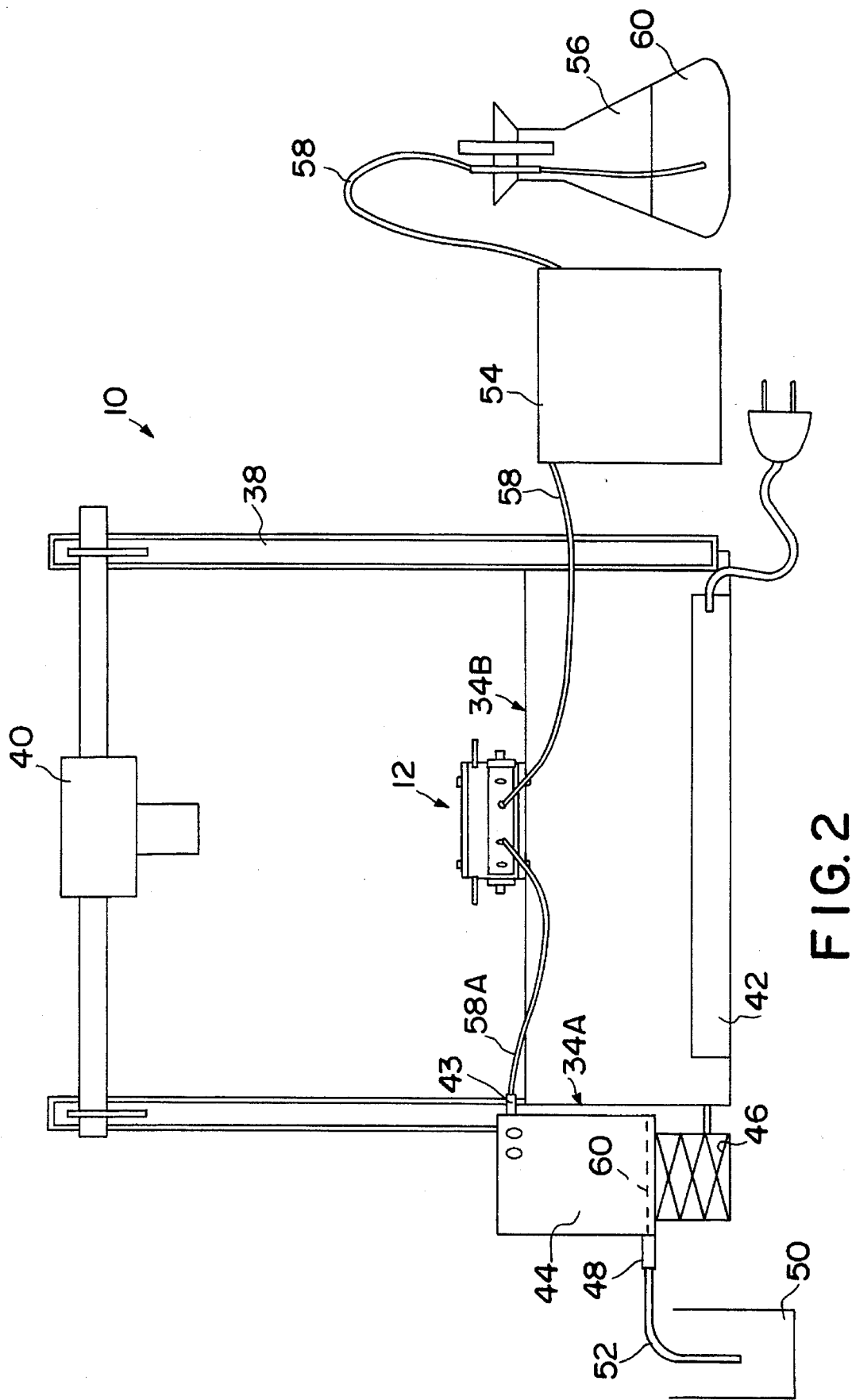
FIG. 2 is a front view of the complete gradient chamber system 10 of one embodiment of the present invention showing the chamber 12, a transilluminator housing 34 with a fluorescent light 42, and an effluent chamber 44 and a waste container 50. A peristaltic pump 54 is connected between the chamber 12 and a feed bottle 56. A camera 40 is mounted onto the transilluminator by a mounting bracket 38.

The present invention relates to a system for recording observations of microorganisms in a controlled environment which comprises: a chamber having a space which supports a semi-solid nutrient medium for the growth of the microorganisms, wherein the chamber has removable spaced apart transparent walls and sidewalls defining a space between the walls and sidewalls; at least two reservoirs for a liquid transport medium to be provided in the chamber, each reservoir with an opening into the space in the chamber; a diffusion membrane in the opening between the reservoir and the opening in the chamber at a height so that the membrane is covered by the semi-solid medium; an inlet into and an outlet from the reservoir for the transport medium; a supply means for supplying the transport medium to the inlet to the reservoir; an effluent means for receiving the transport medium from the outlet of the reservoir; enclosed housing means defining an enclosure and supporting the chamber on an outside portion of the housing means and including a light source inside the housing means for illuminating the chamber through the transparent walls; and recorder means for providing a picture of an activity of the microorganisms over a time span on the nutrient medium as an analyte in the liquid transport medium is fed into the nutrient medium in the space in the chamber through the membrane from the reservoir. Preferably a heating element is used in the housing means to maintain a controlled temperature.

The present invention also relates to a method for the detection of the growth of microorganisms in a controlled environment which comprises: a system for recording observations of microorganisms in a controlled environment which comprises: a chamber having a space which supports a semi-solid nutrient medium for the growth of the microorganisms, wherein the chamber has removable spaced apart transparent walls and sidewalls defining a space between the walls; at least two reservoirs for a liquid transport medium to be provided in the chamber each reservoir with an opening into the space in the chamber; a diffusion membrane in the opening between the reservoir and the opening in the chamber at a height so that the membrane is covered by the semi-solid medium; an inlet into and an outlet from the reservoir for the transport medium; a supply means for supplying the transport medium to the inlet to the reservoir; an effluent means for receiving the transport medium from the outlet of the reservoir; enclosed housing means defining an enclosure and supporting the chamber on an outside portion of the housing means and including a light source inside the housing means for illuminating the chamber through the transparent walls; and recorder means for providing a picture of an activity of the microorganisms over a time span on the nutrient medium as an analyte in the liquid transport medium is fed into the nutrient medium in the space in the chamber through the membrane from the reservoir; and recording the growth of the microorganisms in the space over time using the recorder means.

Figure 3:
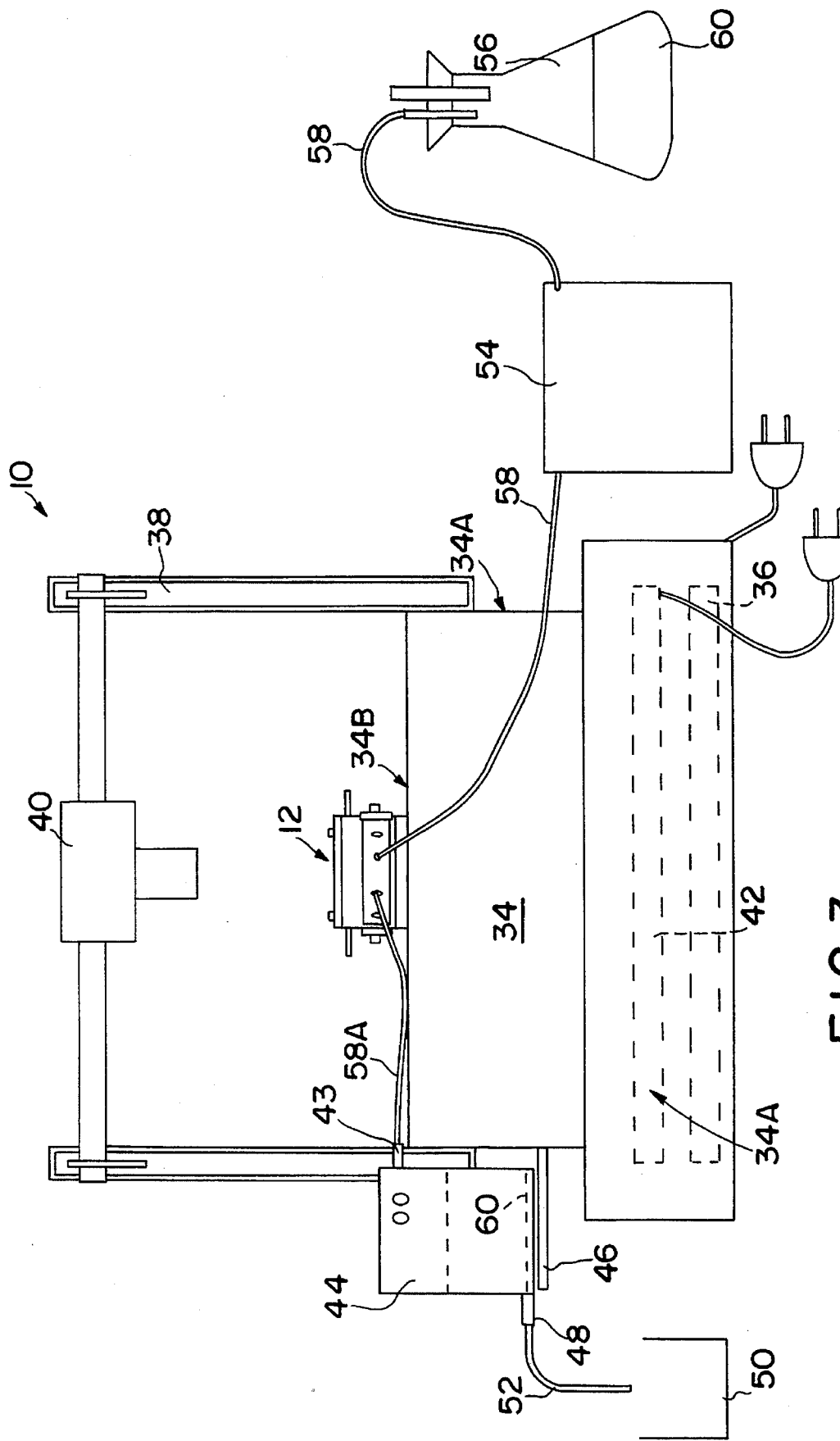
FIG. 3 is a front view of a preferred embodiment of a gradient chamber system 10 showing the chamber 12, a transillumination housing 34, with the effluent chamber 44 and the peristaltic pump 54 connected between the chamber 12 and the feed bottle 56 and the camera 40 mounted to the transilluminator 34 by the bracket 38. A heating element 36 is provided in the transilluminator housing 34.

As shown in FIG. 3, the gradient chamber system 10 is generally comprised of a diffusion gradient chamber 12, a camera 40, a transilluminator box 34 having a fluorescent light fixture 42, a feed bottle 56 and a effluent chamber 44 for waste products. As shown in FIG. 1A, the diffusion gradient chamber 12 has a transparent top plate 12A, a transparent bottom plate 2B and four sides 12C defining an open box shape. The top plate 12A and the bottom plate 12B are mounted onto the top and bottom faces, respectively, and adjacent the sides 12C of the chamber 12. The size of the top plate 12A and bottom plate 12B is such that the outer perimeters of the plates 12A and 12B are flush with the sides 12C of the chamber 12 (FIG. 1B). In the preferred embodiment, the top and bottom plates 12A and 12B are approximately square in shape and have a size of 7.65 cm×7.65 cm×0.6 cm. The top and bottom plates 12A and 12B are provided with a hole (not shown) adjacent to each corner to enable mounting of the plates 12A and 12B into the sides 12C of the chamber 12. The plates 12A and 12B are attached by threaded screws 14 with knurled exposed ends and with threaded ends which extend through the holes in the plates 12A and 12B and into holes (not shown) in the sides 12C of chamber 12. The knurled ends of screws 14 allow for easy removal from and attachment of the plates 12A and 12B to the chamber 12. The plates 12A and 12B are preferably clear polycarbonate which is also used to construct the chamber 12. The chamber 12 is equipped with a gas inlet port 12G and a gas outlet port 12H. The inlet port 12G and outlet port 12H allow a gas to be used in the space 12E defined by walls 12C and plates 12A and 12B so that the chamber 12 can be used under anoxic conditions with an oxygen-free gas or can be used for the inlet of other gases. Thus, the atmosphere of the chamber 12 can be controlled by continuous purging of the headspace with $N_2$ or with oxygen for instance. The gradient chamber 12 preferably has a central arena or space 12E which is preferably 5 cm×5 cm×2.8 cm deep. One of the sides 12C of the chamber 12 is preferably provided with a filler port 16 to enable the central arena 12E to be filled with a gel for supporting the microorganisms.

In the preferred embodiment, the filler port 16 is located in the side 12C of the chamber 12 above the exterior face plate 26 of the reservoir 24 (FIG. 1). Each of the sides 12C of the chambers 12 is provided with a well 12F which is preferably 4.4 cm×1.35 cm×1.0 cm deep at the outside diameter. In the preferred embodiment, the gradient chamber 12 is constructed from a polycarbonate block with the wells 12F machined into each of the four sides 12C of the chamber 12. In an alternate embodiment, the gradient chamber 12 is constructed of ⅛" (0.32 cm) and ³⁄₁₆" (0.48 cm) thick polycarbonate sheets which are bonded together by solvent welding with methylene chloride to form the sides 12C of the chamber 12. The use of transparent polycarbonate to construct the chamber 12 enables microbial growth and migration to be visualized and recorded through the chamber 12. The wells 12F have a lip 12J for providing a seal between a gasket 22 and a reservoir 24 (FIG. 1D). The lip 12J is preferably 2 mm in width. An opening 12I is provided in the well 12F between the central arena 12E and the reservoir 24. The opening 12I allows passage via diffusion of solution 60 from the reservoir 24 into the central arena 12E. The opening 12I between the reservoir 24 and the central arena 12E is preferably 3.8 cm×0.95 cm×0.3 cm. Metal threaded studs 18 located on either side of the opening on the side 12C of the chamber 12 enable mounting of the reservoirs 24 in the wells 12F of the chamber 12. Preferably, the studs 18 are fixed in the side 12C of the chamber 12 by drilling a hole in the side 12C and press fitting a threaded metal sleeve (not shown) into the hole. This construction eliminates the problem of plastic threads which may weaken and tear out, especially when subjected to the high temperatures (120° C.) of autoclaving. A membrane 20 is placed between each opening and its corresponding reservoir 24. The membrane 20 is semipermeable and is preferably constructed of polycarbonate and is cut in the shape of the reservoir 12F with a 10 micrometers thickness and a 0.05 cm pore size. The membrane 20 helps to support the gel and prevents organisms from moving into the reservoirs 24 while allowing diffusion of small molecules into the chamber 12. As shown in FIG. 1A in the preferred embodiment, a gasket 22 is placed between the membrane 20 and the reservoir 24 around the periphery of the membrane 20. The gasket 22 is preferably constructed of VITRON (Fairprene Industrial Products Co., Inc., Fairfield, Conn.) and has a thickness of about 1.0 mm. The gasket 22 ensures a tight seal between the reservoir 24 and the membrane 20.

Preferably, the reservoirs 24 are machined from small blocks of polycarbonate to fit precisely in the wells 12F of the chamber 12. In the preferred embodiment, the inner dimension of the reservoir 24 is about 4.0 cm×0.8 cm×1.0 cm and the outer dimension is about 4.35 cm×1.25 cm×1.0 cm. The reservoir 24 is provided with an external face plate 26 which is mounted onto one side of the reservoir 24 (FIGS. 1A and 1B). The external face plate 26 enables the reservoir 24 to be secured in the well 12F of the chamber 12. The external face plate 26 of the reservoir 24 is preferably rectangular with dimensions of 6.4 cm×1.6 cm×0.7 cm and is provided with two holes (not shown) which are of a size such as to fit the studs 18 in the side 12C of the chamber 12. The external face plate 26 is mounted onto the side 12C of the chamber 12 such that the reservoir 24 extends into the well 12F of the chamber 12 and the studs 18 of the chamber 12 extend through the holes of the external face plate 26. A thumbscrew 28 is screwed onto the stud 18 after the external face plate 26 of the reservoir 24 has been mounted onto the stud 18. The thumbscrews 28 are positioned adjacent the side of the external face plate 26 opposite the reservoir 24. The thumbscrew 28 ensures that the reservoir 24 is sealed in the well 12F of the chamber 12. An inlet tube 30 and an outlet tube 32 are provided in the reservoir 24. Preferably, the tubes 30 and 32 are constructed of stainless steel and are press fitted into the reservoir 24 through the external face plate 26. In the preferred embodiment, the inlet tube 30 has an inner diameter of about 1.0 mm and an outer diameter of about 1.5 min. The outlet tube 32 preferably has an inner diameter of about 2.5 mm and an outer diameter of about 3.0 mm. The outlet tube 32 is located above the inlet tube 30 in the top right corner of the reservoir 24 in order to achieve complete filling of the reservoir 24 without bubble formation.

An additional gas reservoir can be added at the bottom of the chamber 12. The bottom plate 12B of the chamber 12 is then replaced by a silicone membrane 12K with an approximate thickness of 0.5 mm (FIG. 1C). The silicone membrane 12K is very permeable to gases, is transparent and will support the agarose gel. A spacer 12L of approximately 2.5 mm thickness, is placed between the silicone membrane 12K and the bottom plate 12B of the chamber 12. The spacer 12L has an inlet tube 12M and an outlet tube 12N to allow air or any other gas mixture to be flowed through the membrane 12K.

In an alternate embodiment (not shown), a minichamber (not shown), with the same exterior dimensions as the chamber 12 but having a much smaller central arena 12E of a size 2.5 cm×2.5 cm×1.0 cm, is used. This size can give a steady state diffusion gradient in under 48 hours. The wells containing the reservoirs 24 are machined deeper into the minichamber. The internal dimensions of the reservoirs 24 are 2.2 cm×0.6 cm×1.0 cm. Attachment of reservoirs 24 and all other facets of setting up the minichamber are the same as for the full size chamber 12 of FIGS. 1A and 1B.

As shown in FIGS. 2 and 3, each gradient chamber 12 unit is mounted onto a combination transilluminator cabinet or housing 34. The cabinet 34 has sides 34A and an upper plate 34B which is provided with three openings (not shown). Each opening snugly holds one chamber 12 and enables the cabinet 34 to support up to three (3) chambers 12 simultaneously. Preferably, the cabinet 34 is constructed either of stainless steel or an appropriate plastic and is of a size of about 41×27.5×10.5 cm. A heating pad 36 having a thermostated switch (not shown) capable of holding a constant temperature, +/−0.1° C. is mounted in the bottom of the cabinet 34 and provides thermostated temperature control of the gel, allowing constant temperatures of up to 40° C. to be maintained. A mounting bracket 38 is attached to the cabinet 34 and allows a camera 40 to be mounted above the chambers 12 in order to photographically record growth patterns. TV cameras, video recorders and the like can also be used. In addition in the preferred embodiment, the transillumination is also set on an interval time synchronized with the camera 40 interval meter. Alternatively, a micromanipulator (not shown) can be mounted on the bracket 38 to hold microelectrodes for making precisely controlled spatial measurements in the gel. The inside of the cabinet 34 is painted white and is provided with a piece of black felt (not shown) on the bottom of the cabinet 34 in order to provide contrast. A compact fluorescent light fixture 42 is mounted on each of two spaced apart sides 34A of the cabinet 34 to provide a cool, diffuse, even source of fluorescent light from beneath the chambers 12 which is essential to properly visualize microbial growth patterns in the chambers 12. In the preferred embodiment, the light fixture is a 8 watt cool white bulb.

An effluent chamber 44 is mounted onto a stand 46 at one end of the transilluminator cabinet 34 (FIG. 2). The effluent chamber 44 is provided with an outlet 48 and a container 50. The output from the reservoir 24 drains into the input 43 of the effluent chamber 44 and then exits the effluent chamber 44 through the outlet 48 and through tubing 52 into the container 50. The effluent chamber 44 consolidates the output from all the reservoirs 24 into one chamber 44 which in turn drains through the tubing 52 into the container 50. This minimizes tubing requirements and simplifies set-up of the system 10. The transport medium or solution 60 from the reservoirs 24 coming into the inlet 43 drops to the bottom of the effluent chamber 44 providing a sterile barrier due to solution 60 flow. Preferably, the height of the inlet 43 of the effluent chamber 44 relative to the outlet 32 of the reservoir 24 is such as to control the back pressure in the reservoir 24. If there is too much back pressure in the reservoir 24, solution 60 is forced through the membrane 20 and floods the chamber 12 and the gel. If there is too little back pressure siphoning occurs, drawing solution 60 out of the chamber 12 and the gel. In either case, the diffusion gradient is destroyed. Since this passive system eliminates the need to pump solution 60 out of the reservoir 24, it effectively doubles the capacity of a multichannel peristaltic pump 54 used for the system. The pump 54 is used to control the flow rate of the solution 60 into and through the reservoir 24 from feed bottle(s) 56. The feed bottle 56 is preferably either an Erlenmeyer flask or a small carboy. Solution 60 is transported from the feed bottle 56 to the reservoir 24 through tubing lines 58.

One requirement of the gradient chamber 12 is that it is sterilizable by autoclaving at 120° C. For autoclaving, the chamber 12 is assembled and all reservoir inlet tubes 30 are sealed with 1 cm lengths of 0.8 mm inner diameter MARPRENE (Watson Marlow, Inc., Wilmington, Mass.) tubing sealed at one end with silicone. An open end is placed on the inlet tube 30. Outlet tube 32 is sealed by placing TYGON (Baxter Diagnostics, Inc., McGaw Park, Ill.) tubing on the reservoir outlet tube 32 and sealing the open end that connects to the effluent inlet 43 with foil. The tube 58 is also clamped near the open end to prevent any solution 60 loss during the autoclaving. The inlet 43 for the effluent chamber 44 is sealed with short, 1.5 cm, TYGON tubes that are heat sealed at one end. In this way, each unit of the gradient chamber system 10 is able to be autoclaved separately. Alternately, it is possible to attach the tubing lines 58 from the feed bottles 56 directly to the reservoirs 24 prior to autoclaving; however, if two or more chambers 12 are being set up to once, this leads to difficulties because of snarled tubing lines 58. After autoclaving, the chambers 12 are set on the cabinet 34 and the tubing line 58 is connected to the reservoir inlet tubes 30 and the tubing lines 58A are connected to the effluent chamber 44. The agarose stabilized gel is tempered to around 40° C. prior to filling the chamber 12 via the filler port 16 using a 50 ml syringe tipped with a #14 cannula. To test the durability of the chamber 12 to these conditions, the chamber 12 is required to undergo 20 cycles of sterilization and cooling down without any deterioration of the polycarbonate, or loss of structural integrity. Another requirement is that the chamber 12 resist chemicals such as toluene or benzene which are solvents for polycarbonate. The simplest approach to solving this problem is to silicone coat the polycarbonate, which will make it inert to attack by solvents and yet maintain transparency.

IN USE

To set up the gradient chamber 12, the semipermeable membrane 20 is placed in each well 12F of the chamber 12. Next the gasket 22 is placed on top of the membrane 20 and then the reservoir 24 is secured in place in the well 12F. Alternatively, if only one source and one sink are required for an experiment, the other reservoirs 24 are blocked off by replacing the membrane 20 with a solid silicone sheet (not shown) covering the opening 12I. After the chamber 12 has been sterilized and set up, the central arena 12E is filled to a depth of 1.5 cm with molten agarose (0.15%w/v) with a syringe via the filler port 16. The transport of the solutions 60 from the feed bottle 56 to the reservoirs 24 is then started exercising care to remove all air bubbles.

In the preferred embodiment, the total volume of the chamber 12 with the top plate 12A is about 70 ml and the volume of the reservoirs 24 is about 3 ml each. The chamber 12 is filled with 40 ml of gel stabilized medium via the filler port 16 in the side 12C of the chamber 12. Preferably, the chamber 12 is filled with a semi-solid gel that allows microorganisms free movement, but prevents convection. A 1.5 cm thick layer of gel is created that covers the openings 12I between the chamber 12 and the reservoirs 24. One or more test compounds (e.g. substrates, hazardous chemicals, antimicrobial agents, etc.; dissolved in solution 60 basal medium) are next pumped through each reservoir 24, thereby creating a gradient of the particular substance through the gel from the "origin" (i.e. the source reservoir 24) to each of the other "sink" reservoirs 24. Each reservoir 24 on the chamber 12 constitutes a potential "source" for a solution 60 of interest. The remaining reservoirs 24 lacking the particular solution 60 are "sinks" for that compound. Concentration gradients spanning two orders of magnitude across the chamber 12 are achievable. The porous membrane 20 separating the reservoirs 24 from the chamber 12 allows for simple diffusion, but not bulk flow, of small molecules. Each reservoir 24 on the chamber 12 is continually replenished from the feed bottle 56 via the peristaltic pump 54. Molecular diffusion establishes a continuous gradient from high to low concentration between sources and sinks.

In the preferred embodiment, up to four (4) different compounds can be used simultaneously, thereby allowing the creation of as many as four (4) intersecting gradients within the gel in a two dimensional array (i.e. the x and y axes). Obviously, more complex designs (e.g. pentagonal or hexagonal chambers 12) permit creation of more than four (4) individual gradients. In addition, fabrication of chambers 12 with the gas-permeable material 12K (e.g. silicon membrane) separating the chamber 12 from a gas reservoir allows a diffusion gradient of gas (e.g. oxygen) through the gel to be established in the vertical dimension (i.e. the z axis).

Bacteria (not shown) are inoculated either into the gel at a specific point or spread across the surface. Inoculation of the gel with a source of microbes allows the organisms to migrate to positions in the gradients which are conducive to their growth which, in turn, are recognized by the formation of a visible band of organisms, or by the change in color of an indicator dye included in the gel, etc. Moreover, by allowing organisms to form growth zones within an agarose gel-stabilized medium, the microenvironment in and around such zones are characterized by use of microelectrodes, by chemical or enzymatic assays, and by microscopic evaluation of organisms present in the zones of growth or their results can be monitored optically. Although operation of the diffusion gradient chamber 12 is relatively simple, there are several interrelated molecular and microbial activities that add complexity to the system and thus make interpretation of the data challenging. Once the gradient has been established, the cells sense the magnitude of the gradient and move in response to it. However, the cells may also metabolize the chemoattractant, thus affecting the gradient and, hence, their own rate of movement. There interrelated physical and biological events that occur simultaneously within the gradient chamber 12 make it an inherently complex system.

Each reservoir on the chamber constitutes a potential "source" or "sink" for a solution of interest. A continuous solution gradient is then established across the arena from a source to a sink by simple molecular diffusion from a high to low concentration. Within a 4 sided chamber at least 4 intersecting gradients can be established in 2 dimensions (the X and Y axes).

Introduction of cells into the chamber may result in consumption (or production) of substrates, thereby affecting local gradients, and hence, the cells' migration rate. Thus, even though the DGC is relatively simple to use, the interrelated physical and biological events that occur simultaneously within the gradient chamber make it an inherently complex system. For this reason a mathematical model, aimed at predicting the simultaneous biological and physical events taking place in the chamber, has been developed to complement the experimental studies. The model consists of unsteady state conservation equations for the chemoactive compounds, coupled with constitutive equations describing the rates of migration and chemical reaction of these species.

The unsteady state conservation equation describing the simultaneous accumulation, transport, and reaction of the substrate (S) in the semi-solid gel is $$\frac{\partial S}{\partial t} = -\left( i \frac{\partial N_s}{\partial x} + j \frac{\partial N_s}{\partial y} + k \frac{\partial N_s}{\partial z} \right) + r_s = -\nabla \cdot N_s + r_s \quad (1)$$

wherein $N_s$ is the substrate flux vector, $r_s$ is the volumetric production rate of S; t is time; and i, j, and k are unit vectors in the x, y, and z directions, respectively. Because there is no bulk convection of fluid through the semi-solid gel, and the substrate concentrations are presumed to be relatively dilute, the substrate flux can be expressed using the following form of Fick's law of diffusion:

$$N_s = -D\left( i \frac{\partial s}{\partial x} + j \frac{\partial s}{\partial y} + k \frac{\partial s}{\partial z} \right) = -D\nabla s \quad (2)$$

where D is the molecular diffusion coefficient. Combining Equations 1 and 2 gives $$\frac{\partial s}{\partial t} = D\left(\frac{\partial^2 s}{\partial x^2} + \frac{\partial^2 s}{\partial y^2} + \frac{\partial^2 s}{\partial z^2}\right) + r_s = D\nabla^2 s + r_s \quad (3)$$

Boundary conditions need to be specified in order to calculate the concentration profiles across the gel. The membrane between the liquid reservoir and the gel may provide a significant resistance to substrate mass transfer. This effect may be mathematically described using a convention boundary condition:

$$Ns = -D\nabla s = K_2(s_r - s_i) \quad (4)$$

where $k_s$ is the mass-transfer coefficient, $s_r$ is the bulk substrate concentration in the reservoir, and $s_i$ is the substrate concentration in the gel adjacent to the membrane. The mathematical model was solved using a finite-difference approach on a Convex C-220 supercomputer. All calculations were performed with double precision. To verify the computer model, the computer simulations were compared with analytical solutions of Equations 3 and 4 for the limiting case of one-dimensional, unsteady state substrate diffusion without reaction.

Materials and Methods

Chemical gradients. Initial experiments were done to test the capacity of the chamber 12 for establishing gradients. Two of the test compounds used were glucose and pyruvate, because they were physiologically relevant and there are rapid and sensitive enzymatic assays for quantitating them. For these experiments there was one source reservoir 24 and one sink reservoir 24 180° opposed to one another. The two side reservoirs were sealed off by substituting a piece of silicone sheeting (Silastic, Dow Chemical Co., Midland, Mich.) for the filter membrane 20. The source feed (Solution 60) contained approximately 10 mM substrate dissolved in 300 to 1000 ml (depending on the duration of the experiment) of deionized $H_2O$ (d-$H_2O$); the sink feed contained only d-$H_2O$. The gel in the chamber contained d-$H_2O$ and 0.15% agarose (Bethesda Research Laboratories, Bethesda, Md.). Neither the feed solutions, nor the chamber were autoclaved for these experiments; instead KCN, 0.01% (w/v) was added to both the gel and the source feed to prevent contamination. The chamber 12 was set-up with appropriate feeds as described above. At given time periods, the chamber top. plate 12A was removed and samples of the agarose gel were taken at points along a transect (measured with a ruler) down the middle of the gradient chamber starting at the side of high concentration. For sampling a 25 gauge needle on a 1 ml syringe was used. The samples were stored in Eppendorf tubes at $-20°$ C. until analysis. The maximum sample size was 200 µl. For enzyme assays, the samples were melted in a microwave and subsampled while still warm with a pipettor to ensure accurate volume measurement of the agarose. Enzyme assays were carried out using commercial assay kits from Sigma Chemical Co., St. Louis, Mo.; glucose was quantitated by reaction with glucose oxidase/horseradish peroxidase (Sigma Chemical Co.); pyruvate was determined by NADH conversion by lactate dehydrogenase.

Response to *E. coli* to gradients. The following *E. coli* strains with relevant phenotype and genotype were used: HCB 33=RP437, wild type, str$^r$; HCB 137=RP3098, non-motile, fla- (Δflal–flaH), str$^r$; HCB 437, nonchemotactic, runs only (ΔMotA–motB), str$^r$; HCB 483, nonchemotactic, runs and tumbles (ΔcheA–cheZ). These strains were maintained on either tryptone medium or M63 minimal salts with 10 mM glycerol. For *E. coli* strains the M63 medium was supplemented with the amino acids required for growth (histidine, leucine, methionine, and threonine), and streptomycin as described previously (Wolfe, A. J., and H. C. Berg, Proc. Natl. Acad. Sci. USA 86:6973–6977 (1989)). For chemotaxis experiments with *E. coli* in the gradient chamber, the M63 medium supplemented with the amino acids (2 µg/ml) and 2 mM glycerol was used as the base medium for source and sink feeds as well as in the gel stabilized medium in the arena. The gel stabilized medium only, contained 125 µg/ml streptomycin. The source feed only contained the chemoattractant. The chambers 12 were autoclaved and set up as described above and the feeds were started through the reservoirs 24 at a flow rate of 2.5 ml/h. For all growth experiments the gradient chambers 12 were set up in a 30° C. constant temperature room. After the gradient was allowed to establish for 12–20 h, the chamber 12 was inoculated in the center with a mid to late log phase culture of *E. coli* grown overnight in M63 medium with 10 mM glycerol at 30° C. Inoculation was accomplished by lifting the top off the chamber 12 and quickly inserting a pipet tip containing 7.5 µl of culture to the bottom of the agarose and then withdrawing it and expelling the inoculum simultaneously. The top plate 24 was replaced immediately. To ensure central inoculation, a small black reference mark was made on the bottom plate of the chamber that showed dead center. After inoculation, photographs were taken at regular intervals using camera 40.

Separation of *E. coli* and *P. fluorescens*. For these experiments *E. coli* HCB 33 and *Pseudomonas fluorescens* (ATCC B-13525) were used. Three gradient chambers were set up in parallel using the M 63 medium with 2 mM glycerol and amino acids, as described above; streptomycin was omitted. Each chamber 12 received opposed gradients of 0.1 mM aspartate and 0.25 mM valine. The two side reservoirs 24 were sealed off. The gradients were allowed to establish for 18 hour prior to inoculation. *P. fluorescens* and *E. coli* were grown overnight on M63 medium with 10 mM glycerol to an OD 600 nm of 0.48 and 0.40, respectively. One chamber 12 was inoculated with 2.5 µl of *P. fluorescens*, one chamber 12 was inoculated with 2.5 µl of *E. coli*, and one chamber 12 was inoculated with 5 µl of a 1:1 mixture of the two bacteria. Growth and migration patterns were recorded photographically. When it visually appeared that good separation of the two bacteria had occurred, 10 µl samples were taken aseptically with a pipettor from selected points in the gel and diluted and spread plate in duplicate onto tryptone medium. Two sets of spread plates were made for each sampling site one that contained streptomycin and one that did not. The plates were incubated for 48 h at 30° C. and colony forming units CFUs were determined. To differentiate between *E. coli* and *P. fluorescens*, the difference in CFUs between medium with streptomycin and without were compared. In addition, 20 random colonies were picked from each set of plates from each site and tested for their oxidase reaction using a commercially available oxidase reagent (Difco Laboratories, Detroit, Mich.).

Photography. For photography, a 35 mm camera 40 was used, most experiments were done using a Canon Ft-b. For later experiments a Minolta Maxxum 7000i equipped with an interval timer and autowinder that permitted automatic exposure at a preset interval was used. In the latter case, the transilluminator cabinet 34 was also set on an interval timer synchronized with the intervalometer of the camera 40. The lights were turned on one minute prior to the exposure time and turned off one minute after. Kodak T-MAX 400 black and white print film was used at ASA 800, the exposure time was f 9.5, 1/60 sec. To determine the rates of migration a time series of negatives from an experiment were printed to exactly the same size, and then measurements were made directly from the prints with calipers to the nearest 0.1 mm. The rates were then corrected for magnification by the enlargement process to give actual values. For all reported time series, time zero was considered the time of inoculation and not the time the gradient was initiated.

Chemicals. For chemotaxis experiments chemically synthesized L-aspartic acid, L-valine, and L-serine purchased from K&K Fine Chemicals (Costa, Mesa, Calif.) were used. All other chemicals were of reagent grad.

Establishment of Gradients and Mathematical Model. Each reservoir 24 on the chamber 12 constitutes a potential "source" for a solution of interest. The remaining reservoirs 24 lacking the particular solution are "sinks" for that compound. Within a 4 sided chamber up to 4 intersecting gradients can be established in 2 dimensions (x-y).

EXAMPLE 1

Randomly selected chambers 12 were examined for uniformity of construction by determining the profile of pyruvate gradients established in them after 5 days. Pyruvate gradients were similar in the three different chambers 12.

Figure 4:
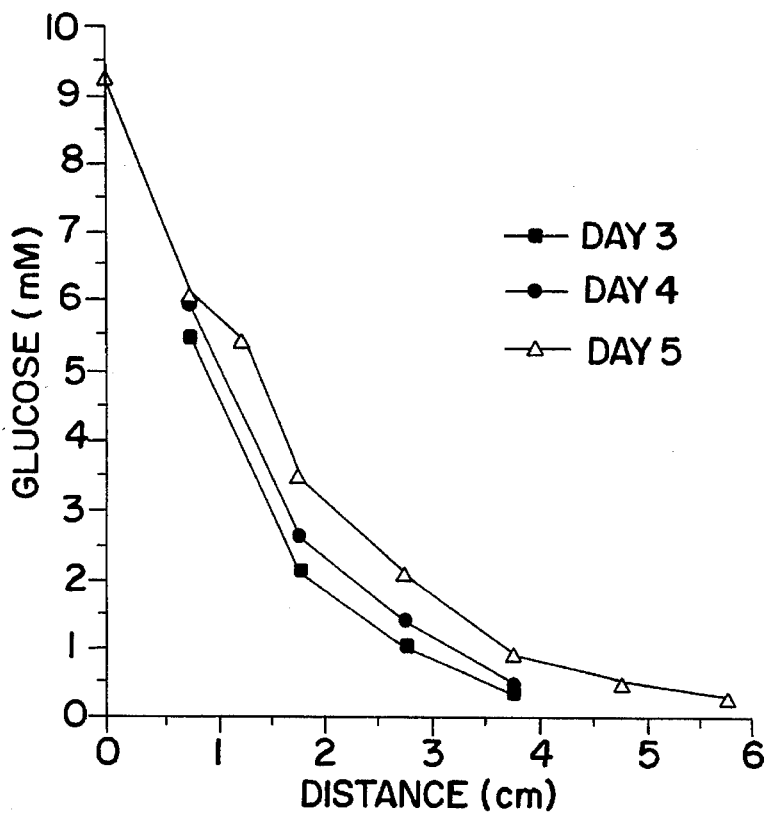
FIG. 4 is a graph showing the time course measurement of a diffusion gradient of glucose established from one of the reservoirs 24 in the diffusion gradient chamber 12 (position "zero" on x-axis). The starting concentration of glucose was 9.4 mM, samples were removed from the gradient chamber 12 at day p3 and day 4; on day 5 the experiment was ended and more extensive sampling was done. The temperature during the experiment was maintained at 27° C. (+/−1°) using the system of FIG. 3. Note that at all times the gradient was curvilinear.

Establishment of chemical gradients. A number of experiments were done to establish the best means of setting up a gradient. To test the mathematical model, glucose was chosen as a model substrate. The value of $k_s$ was determined experimentally by fitting the model to the glucose profile shown in FIG. 4. The diffusion coefficient used in these calculations was $6.7 \times 10^{-6}$ cm$^2$/s. The value has been measured for glucose in d-H$_2$O at the same temperature, and previous studies have shown that the diffusional flux of small molecules like glucose is virtually unaffected by the presence of highly porous, cross-linked immobilization supports such as 2% calcium alginate (Hannoun and Stephanopolous, Biotechnology and Bioengineering Vol. SSVII, 829–835 (1986)). The mass transfer coefficient for transport across the membrane that optimized agreement between the model prediction and experimental data for the 5 d curve was $1.3 \times 10^{-5}$ cm/s.

Figure 5:
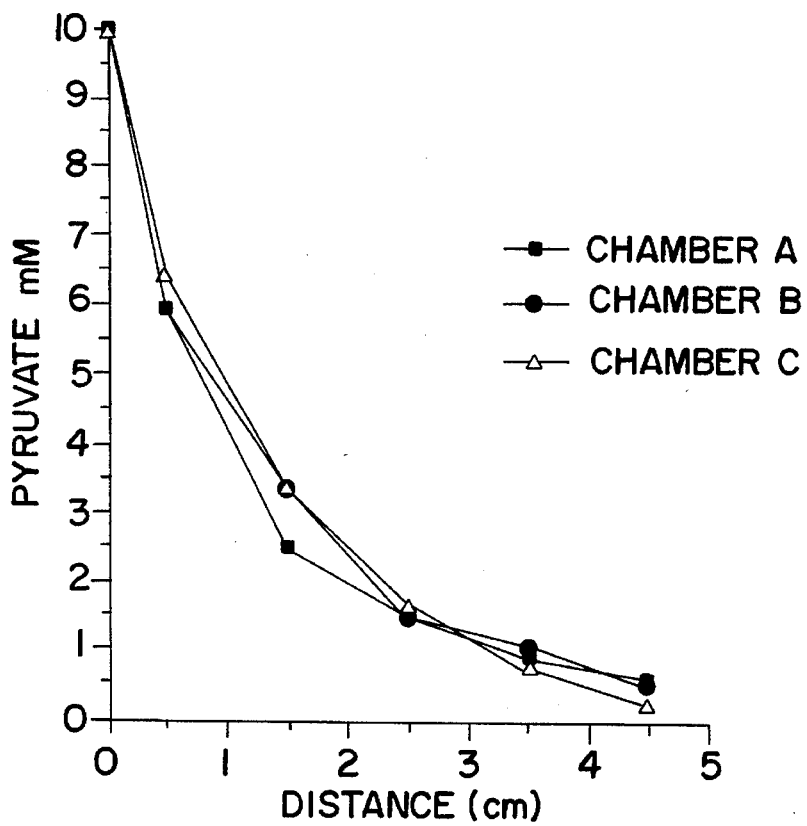
FIG. 5 is a graph showing replicate gradients of pyruvate established in three separate gradient chambers 12. Three chambers 12 were run in parallel using the same 10 mM sodium pyruvate feed supply from reservoirs 24. The chambers 12 were left undisturbed for 5 days and then sampled for pyruvate concentration. The temperature during the experiment was maintained at 27° C. (+/−1°) using the system of FIG. 3.
Figures 6A, 6B, 6C, 6D, 6E:
FIGS. 6A to 6E are photographs showing the response of E. coli HCB 33 to an aspartate gradient. Aspartate (0.1 mM) was introduced from the reservoir on the S side of the chamber 12 of FIG. 3. On the N side was a sink reservoir containing a glycerol and salts solution, but no attractant; the E and W sides were sealed off. The chamber 12 was inoculated in the center with E. coli cells 20 h after the gradient was initiated. The time of inoculation is considered as time zero. Note that the front moving S (up gradient) is diffuse while the band moving N forms a well defined front. Also note the rapid tangential spread of cells in the SE and SW directions.

The mathematical model was then used to predict the progression of the substrate concentration front across the gel slab. The steady-state profile is approached asymptomatically; however, approximately 2 weeks are required for the substrate glucose to reach 95% of its steady-state value throughout the gel. Thus, the experiments reported here were begun with substrate gradients that differed somewhat from the steady-state gradients. In terms of the empirical dynamics of a gradient across the chamber, 5 cm in this case, the gradient covered about two orders of magnitude. With 10 mM starting concentration, it took about 4 days for a detectable amount of glucose (>10 µM) to reach the opposing sink. It took approximately 24 hours for a detectable concentration to reach the center of the chamber (data not shown). To determine that the results between chambers 12 were reproducible, pyruvate gradients were run in 3 replicate gradients. FIG. 5 shows that the results are reproducible.

EXAMPLE 2

Figure 7:
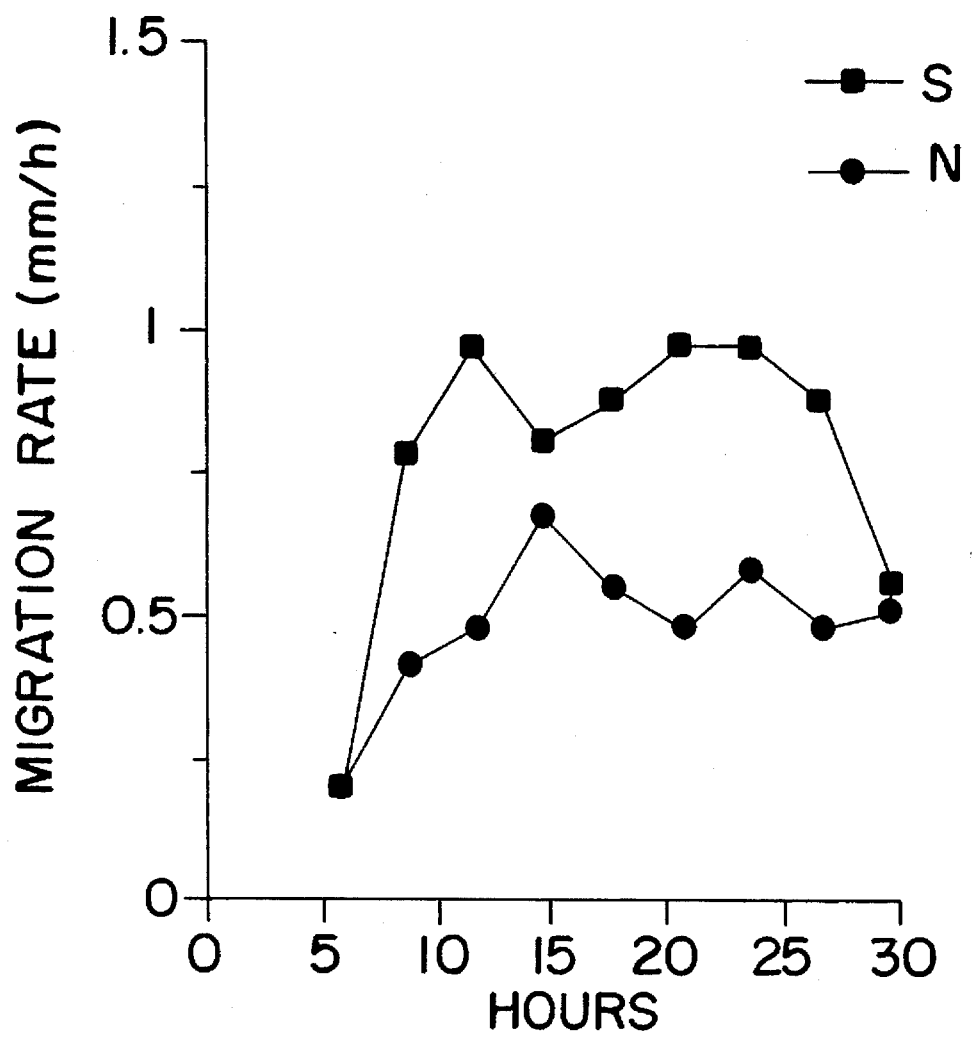
FIG. 7 is a graph showing migration rates of E. coli cells in an aspartate gradient. These rates were plotted from data obtained in the experiment shown in FIG. 6. The rate of the front moving S toward aspartate is appreciably faster than the rate moving N away from aspartate.
Figure 8A:
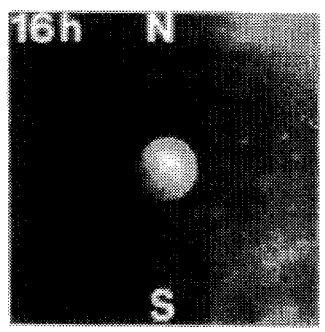
FIGS. 8A to 8C are photographs showing the response of E. coli HCB 33 to a gradient of alpha-methyl aspartate in the system of FIG. 3. The alpha-methyl aspartate, 0.5 mM was introduced from the reservoir 24 on the S side of the chamber 12. The N, S and W sides are as described in the legend to FIG. 6. The chamber 12 was inoculated in the center with E. coli cells 20 h after the gradient was initiated. Note that there is a small bias toward the alpha-methyl aspartate, and that the migrating fronts are well defined at all times.
Figure 8B:
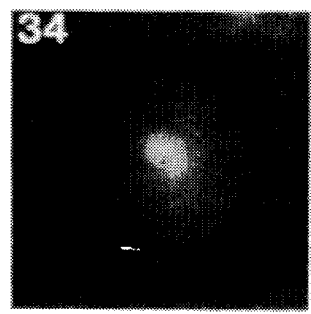
Figure 8C:
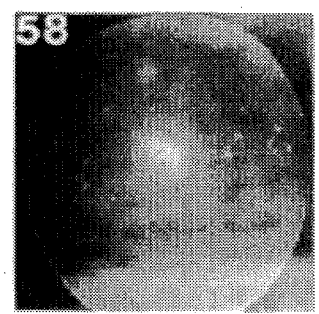

The response of *E. coli* HCB 33 to an imposed gradient starting with 0.1 mM aspartate is shown in FIGS. 6A to 6E. The time series of photographs showed the cells have grown and migrated more rapidly up the aspartate gradient (S) toward the source than in the opposing direction (N) toward the sink. In the SE and SW directions, there was also more rapid migration. The migration rates of the different fronts for this experiment are plotted in FIG. 7. The rate increased initially and then reached a plateau of 1.0 mm/h before slowing again as the cells approached the aspartate source. In the direction away from the aspartate the rate of movement due to random motility is measured. An average rate of 0.56 mm/h occurred toward the sink. This compared favorably with a rate of 0.64 mm/h for an experiment in which HCB 33 was exposed to a static concentration of 2 mM glycerol without attractant. In this latter case, the cells grew as a concentric ring out from the point of inoculation (results not shown). There was also a difference in the structure of the migration fronts. Towards aspartate, the more rapidly moving front was a diffuse band, while in the N direction the front formed a sharp well-defined band. The rapid migration in the SE and SW directions was intriguing because the aspartate gradient should be very shallow tangential to the source; however, if the cells consumed aspartate they would create a steeper, self-imposed gradient in this orientation to which they might respond. To test this, *E. coli* was exposed to a gradient of alpha-methyl aspartate, a nonmetabolizable analog of aspartate. The results are shown in FIGS. 8A to 8C. In this case, there was only a small bias up the alpha-methyl aspartate gradient in the S direction, in all other directions there was concentric growth and migration of cells out from the inoculation point. The average rate of migration from 16 to 47 h in the direction of alpha-methyl aspartate (S) is 0.51 mm/h, while in the opposite direction the rate is 0.46 mm/h. Integrated over this time period, this difference may not be statistically significant; however, in several experiments there was always a small bias toward a-methyl aspartate.

EXAMPLE 3

An experiment that compared the chemotactic response to serine and aspartate, indicated that different growth and migration patterns resulted from the different amino acids as shown in FIGS. 9A to 9H. As would be predicted, based on threshold response concentrations for serine and aspartate $1 \times 10^{-7}$ and $3 \times 10^{-8}$, respectively (Macnab, R. M., Motility and chemotaxis. in: *Escherichia coli* and *Salmonella typhimurium* (F. C. Neihardt, et al. eds) ASM (1987)), *E. coli* should perceive and bias its random walk toward aspartate sooner than toward serine. Indeed this is the case, 10 h after inoculation, the cells showed a strong bias to aspartate (FIGS. 9A to 9D), while cells responding to serine did not show a strong bias until 16 hours after inoculation (FIGS. 9E to 9H). The average rate of migration from 10 to 24.5 h towards aspartate was 1.2 mm/h and for serine was 0.9 mm/h. The peak rate toward aspartate was 1.6 versus 1.45 mm/h toward serine. The gross morphology of the growth patterns also differed, For aspartate there was more rapid SE & SW migration, while the bias toward serine was wholly in the S direction. Thus, information may be gained from both the shape of a growth pattern in the gradient chamber as well as from the rates at which migration fronts move.

EXAMPLE 4

Figure 10A:
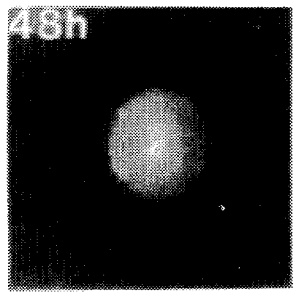
FIGS. 10A to 10C showing response of motility and chemotaxis impaired mutants of E. coli to aspartate. Three chambers 12 were run in parallel with 0.1 mM aspartate coming from the S reservoir 24 using the system of FIG. 3. N, E, and W reservoirs 24 were as described in the legend to FIG. 6. The chambers 12 were inoculated in the center with cells 20 h after the gradient was initiated. The results for each strain are shown 48 h after inoculation. In the left panel is HCB 483, deleted for chemotaxis genes but able to run and tumble; in the center panel is HCB 437, also deleted for chemotaxis genes, but able to run only; in the right panel is HCB 136 an immotile mutant.
Figure 10B:
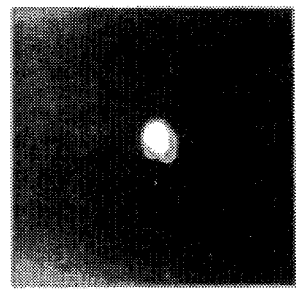
Figure 10C:
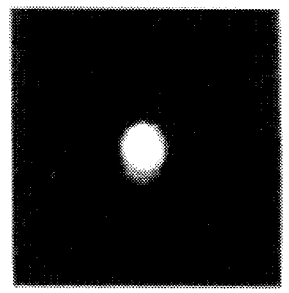

To demonstrate that both motility and chemotaxis were important to the growth and migration patterns of bacteria in the chamber, *E. coli* mutants in chemotactic response or motility were tested for their response to aspartate gradients. The results of these studies are illustrated in FIGS. 10A to 10C. Strain HCB 483, which is negative for chemotaxis genes but maintains the capacity to run and tumble, migrated concentrically from the point of inoculation (FIG. 10A) as would be predicted for a case where there is no bias in a random walk due to chemotaxis. The average rate of migration for this strain is 0.16 mm/h, much slower than the rates calculated for HCB 33. The strain HCB 437 is also gutted for chemotaxis genes and is motile; however, its flagella only spin counterclockwise (CCW). Thus it executes runs but no tumbles. This strain grew but did not migrate appreciably from the inoculation point (FIG. 10B). The same was true for strain HCB 137 which is immotile due to lack of flagella (FIG. 10C).

EXAMPLE 5

Separation of *E. coli* HCB 33 and *P. fluorescens*. To demonstrate that bacteria could be separated based upon on their motility and chemotactic responses, advantage was taken of the fact that valine is a repellent and aspartate an attractant for *E. coli* and that *P. fluorescens* responds neither positively nor negatively to either of these amino acids at the concentrations used. Thus *E. coli* should move rapidly toward aspartate but be inhibited by valine, while p. fluorescens will move with a random bias toward both amino acids. The results are shown in FIGS. 11A to 11I. The control chamber with HCB 33 alone showed that the organism responded markedly to aspartate. The average rate was 1.0 mm/h, but its movement up the valine gradient is arrested after approximately 20 h. P. fluorescens alone moved concentrically from the point of inoculation at a rate of 0.81 mm/h. It was noticeable that *P. fluorescens* formed 2 concentric rings, an inner band that formed at the surface of the agarose, and an outer band that was at depth in the agarose. Both bands moved at nearly the same rate. This could be a response to oxygen, or a surface effect. In experiments in which the semisolid gel had a thin (1–2 mm) overlayer of 1% agarose only one band formed (results not shown). When the two organisms were mixed in a 1:1 ratio (FIGS. 11D to 11G) and inoculated in the opposed gradients, the two patterns were essentially superimposed upon one another. As a result of its biased random walk towards aspartate the *E. coli* moved more rapidly in this direction and dominated over *P. fluorescens*. However, *P. fluorescens* was not inhibited by the valine and migrated steadily in direction of the valine gradient and thus dominated in this region of the gel. Plating results revealed only $str^r$, oxidase—colonies along the northern edge of growth. A sample taken approximately 1 cm N of the center of the chamber indicated a predominance of $str^r$ cells, but 2 of 20 colonies tested were oxidase +. A sample from the southern edge of growth showed only $str^s$ cells and all the colonies were oxidase +.

In relation to Examples 1 to 5:

(1) Gradient Conditions. Solution gradients established in the chamber 12 are continuous and quantifiable based on the laws of Fickian diffusion. The mathematical model fits empirical data well. An important finding is that the polycarbonate membrane 20 acts as a significant barrier to diffusion. This causes a larger drop in concentration across the membrane 20 from the source into the gel. Concurrently, the membranes separating the gel from the sink(s) act as a dam maintaining higher concentrations of diffusible substances in the gel. This has ramifications for some long term experiments, or certain types of gradients. Another important consideration is that, due to the cross sectional area of the chamber 12, it is not temporally practical to establish steady state conditions prior to initiating an experiment. Because the system is not at steady state, the slope of the gradient will change with time as the gradient approaches steady state. However, since the approach to steady state is asymptotic, the change in concentration at a given point decreases exponentially. These changes may be negligible compared to the range of concentrations that bacterial sensory and uptake systems are responsive to, which can often span orders of magnitude (Bourret, et al, Annu. Rev. Biochem. 60:401–441 (1991)). Of course, when cells are introduced into the chamber 12 they can alter the shape and fluxes of gradients in accordance with their uptake and metabolism of the diffusible compounds. An advantage of the continuous nature of the gradient is that as in a chemostat, very low substrate concentrations can be used thus simulating nature better. The "minor" or small chambers are capable of establishing steady state gradients within 72 hours, which is an advantage.

(2) Chemotactic Response of *E. coli*. The primary conclusion from Examples 2 to 5 with *E. coli* is that it behaves largely as it should to imposed gradients of chemoattractant in the gradient chamber. The results confirm those of Wolfe and Berg (Wolfe, A. J., and H. C. Berg. Proc. Natl. Acad. Sci. USA 86:6973–6977 (1989)) who used static swarm plates with soft agar to study the response of similar strains of *E. coli* to aspartate. The results show that with aspartate, the microbial population exhibits a strong migrational bias up the gradient of attractant. When the gel is inoculated within 24 hours after initiating the gradient the concentration at the center should be zero, thus growth and movement of cells begins with no bias. As the aspartate concentration reaches the threshold for detection by *E. coli* ($3 \times 10^{-8}$M) the cells respond with a bias toward the aspartate, the rate of migration reaches a plateau and then falls as the cells approach the source where the aspartate concentration approaches saturation for the aspartate receptors, approx. $1 \times 10^{-4}$M (Wolfe, A. J., and H. C. Berg, Proc. Natl. Acad. Sci. USA 86:6973–6977 (1989)). When higher starting concentrations of aspartate were used to initiate gradients the distance the cells migrated chemotactically before returning to the non-biased random rate of migration decreased correspondingly.

Based on the patterns of growth and movement of cells, it is apparent that growth and consumption are important to the extent of the response and the shape of the growth pattern. When the nonmetabolizable analog of aspartate, a-methyl aspartate is the attractant, the amount of bias is significantly decreased and is only oriented perpendicular to the direction of the gradient. Serine, which can be taken up and metabolized by *E. coli* may represent an intermediate case, where there is a strong bias perpendicular to the gradient, but little bias tangentially. Whether the lack of tangential bias is due to limited uptake of serine or less sensitivity of the chemosensory apparatus for serine or a combination of these two effects will require more study. Apparently metabolism of aspartate is rapid enough to create sufficiently steep lateral gradients of attractant so that the cells respond with a tangential bias as well.

The random rate of cell movement is obtained from the migration rate toward the opposing sink without chemoattractant. The measurement of migration rates also suggests that growth is important in affecting the rate. In all cases the rates of both random and directed cell migration increased initially, possibly in response to growth and increased bacterial density. The fact that the front of cells moving rapidly up an attractant gradient form a diffuse band, while cells from the same population moving at random form a sharp band is interesting. One explanation may be that cells moving toward an attractant will exhibit longer runs and fewer tumbles than nonchemotaxing cells. This may effectively broaden the front for chemotaxing cells. If the cells are migrating at a rate that is rapid relative to their growth rate there may be a dilution effect at the front which will make it appear more diffuse. Microscopic observations of cells from bands moving towards the source and the sink revealed actively chemotactic cells to be more active; although the observed differences were not striking.

Mutants in chemotaxis and motility showed the importance of these traits for movement of cells in the agarose. As expected, nonmotile mutants spread very slowly by growth only. A mutant strain that runs only also did not translate through the agarose, it has been suggested that such a mutant may get trapped in the agarose matrix since it cannot reorient itself (Wolfe, A. J. and H. C. Berg, Proc. Natl. Acad. Sci. USA 86:6973–6977 (1989)). A mutant without chemotaxis genes but able to run and tumble did migrate through the agarose, but showed no bias to aspartate and moved at a slower rate than did wild type cells.

(3) Separation of Bacteria. Example 5 demonstrated that it is possible to separate two organisms based on differences in their response to gradients of potential attractants and repellents. While this experiment was not specifically designed as a competition experiment it also demonstrated that chemotaxis may give an organism a competitive advantage. Theoretical calculations have postulated that chemotaxis should lead to competitive advantage in some cases (Kelly, et al., Bacterial Chemotaxis and Microbial Competition, 16, 115–131 (1988)). In this case, both organisms had similar growth rates on glycerol; however, the *E. coli* was an auxotroph requiring four amino acids, while the *P. fluorescens* is a prototroph which should give it a growth advantage since it could eliminate the *E. coli* strain by consuming the amino acids it requires. However *E. coli*'s sensitive response to aspartate led it rapidly into fresh medium so it could dominate in regions where it was attracted to aspartate.

Use of System

Clearly the gradient chamber has uses for studying chemotaxis in bacteria. An especially fruitful area of use of multiple gradients is to study how organisms respond to conflicting signals, either attractant and repellent or attractants in the presence of nutritional stress such as low phosphate or nitrogen. Another application is studying environmental control of gene expression where reporter genes are linked to a gene of interest. Using this approach, the response of individual genes as well as of organisms to gradients of effector molecules can be studied. The system can be used to study anaerobic bacteria because it can be operated in the absence of oxygen.

The method allows the isolation of organisms with potentially novel properties. For instance, gradients of NaCl and toluate have been used in order to investigate the efficacy of the gradient chamber for isolating halotolerant or halophilic bacteria capable of using toluate and related aromatic hydrocarbons. Using a soil sample contaminated with oil brine as an inoculum in a gradient chamber 12 with salt and toluate gradients set at 90° to one another, distinctive patterns of growth form that respond to the different gradients. The chamber 12 provides information about the general community response to these conditions, about synergistic effects of the dual stress of high salt and aromatic compound, and the response of individual organisms which may begin to grow as flares out into inhospitable territory. In addition it has been possible to isolate a number of organisms capable of growing on salt and toluate from the chamber.

It is possible to separate defined mixed populations of bacteria on the basis of their chemotactic behavior in the diffusion chamber 12. Optimum parameters for routine operation of the chamber 12 can be determined (i.e. gel strength; solution concentration; inoculation site and strategy, etc.), as well as define the responses of well characterized bacteria in the chamber 12. Studies with *E. coli* strains, some of which have known impairments in their chemosensory or motility system can be made. The results facilitate interpretation of behavioral responses exhibited by less well-characterized bacteria, as well as mixed microbial communities. Inasmuch as little is known about directed movement of bacteria through agar gels these studies can increase basic knowledge of migratory behavior of bacteria in viscous and semisolid habitats. Additional refinements in the quantitative use of the chamber 12 include: application of microsensors for analysis of physicochemical conditions directly in the diffusion gradient; computer image analysis of growth and migration patterns of bacteria; and mathematical analysis and modeling of bacterial growth and behavior in multiple diffusion gradients.

It is intended that the foregoing description be only illustrative of the present invention and that the present invention be limited only by the hereinafter appended claims.

We claim:

1. An apparatus which functions for recording observations of microorganisms in an environment by providing a diffusion gradient in the environment which comprises:

(a) a chamber having a space which supports a semi-solid nutrient medium for microorganism growth, wherein the chamber has spaced apart transparent walls and sidewalls defining a space between the walls;

(b) at least two reservoirs mounted on the chamber for a liquid transport medium to be provided in the chamber each reservoir with an opening into the space in the chamber through an opening into the chamber, wherein the reservoirs are removably mounted on the chamber;

(c) a diffusion membrane mounted between the opening in the reservoir and the opening in the chamber at a height so that the membrane is covered by the semi-solid nutrient medium wherein the diffusion membrane allows a molecule in the transport medium through the opening in the reservoirs, the diffusion membrane and the opening in the chamber into the semi-solid nutrient medium to establish the diffusion gradient of the molecule in the chamber for the microorganism wherein one of the reservoirs can serve as a sink to receive the molecule moving from the semi-solid nutrient medium out of the diffusion gradient;

(d) an inlet into and an outlet from each of the reservoirs for flow of the liquid transport medium;

(e) a supply means for supplying the liquid transport medium to the inlet to each of the reservoirs;

(f) an effluent means for receiving the transport medium from the outlet of each of the reservoirs without destroying the diffusion gradient of the molecule in the semi-solid nutrient medium;

(g) enclosed housing means defining an enclosure and supporting the chamber on an outside portion of the housing means and including a light source inside the housing means for illuminating the chamber through the transparent walls; and (h) recorder means for providing a picture of an activity of the microorganisms over a time span on the nutrient medium as an analyte in the liquid transport medium is fed into the nutrient medium in the space in the chamber through the membrane from each of the reservoirs.

2. The apparatus of claim 1 wherein the recorder means is a camera.

3. The apparatus of claim 1 wherein the light source and the recorder means cooperate together for the recording.

4. The apparatus of claim 1 wherein at least one of the transparent walls of the chamber comprises a sheet permeable to a gas.

5. The apparatus of claim 1 wherein the chamber is composed of a polycarbonate.

6. The apparatus of claim 1 wherein a heating means is provided in the housing means for regulating a temperature of the chamber.

7. The apparatus of claim 1 wherein the reservoirs are provided on opposed side walls of the chamber.

8. The apparatus of claim 1 wherein the side walls of the chamber are rectangular and wherein a reservoir is mounted on each of the side walls.

9. The apparatus of claim 1 wherein the recorder means is a camera and the camera and the light source cooperate together for the recording.

10. The apparatus of claim 9 wherein a heating means is provided in the housing means for regulating the temperature of the chamber.

11. The apparatus of claim 10 wherein the reservoirs are mounted on recesses in the chamber.

12. The apparatus of claim 11 wherein the sidewalls of the chamber are rectangular.

13. The apparatus of claim 12 wherein the reservoirs are mounted in the recesses in the sidewalls of the chamber.

14. The apparatus of claim 13 wherein a seal is provided between the membrane and the reservoir.

15. The system of claim 1 with gas supplying means for regulating an atmosphere in the chamber.

16. The apparatus of claim 1 wherein the housing means contains a temperature control means for regulating a temperature of the chamber.

17. The apparatus of claim 1 wherein an effluent chamber is provided to collect the transport medium from the outlet of the reservoir and provide a back pressure to prevent siphoning of the transport medium from the semi-solid nutrient medium.

18. The apparatus of claim 1 wherein tubes connect the reservoirs to the effluent means and wherein a height of the effluent means relative to the reservoirs provides a back pressure in the reservoirs through the tube to maintain the diffusion gradient.

19. The apparatus of claim 18 wherein the effluent means is an effluent chamber which collects the transport medium from the reservoirs and provides the back pressure.

20. A method for the detection of the growth of microorganisms in an environment by providing a diffusion gradient in the environment which comprises:

(a) providing an apparatus which is a system which comprises: a chamber having a space which supports a semi-solid nutrient medium for the growth of the microorganisms, wherein the chamber has spaced apart transparent walls and sidewalls defining a space between the walls; at least two reservoirs mounted on the chamber for a liquid transport medium to be provided in the chamber each reservoir with an opening into the space in the chamber through an opening into the chamber, wherein the reservoirs are removably mounted on the chamber; a diffusion membrane mounted between the opening in the reservoirs and the opening in the chamber at a height so that the membrane is covered by the semi-solid nutrient medium wherein the diffusion membrane allows a molecule in the transport medium through the opening in the reservoirs, the diffusion membrane and the opening in the chamber into the semi-solid nutrient medium to establish the diffusion gradient of the molecule in the chamber for the microorganism wherein one of the reservoirs serves as a sink to receive the molecule moving from the semi-solid nutrient medium out of the diffusion gradient; an inlet into and an outlet from each of the reservoirs for flow of the liquid transport medium; a supply means for supplying the liquid transport medium to the inlet to each of the reservoirs; an effluent means for receiving the transport medium from the outlet of each of the reservoirs without destroying the diffusion gradient of the molecule in the semi-solid nutrient medium; enclosed housing means defining an enclosure and supporting the chamber on an outside portion of the housing means and including a light source inside the housing means for illuminating the chamber through the transparent walls; and recorder means for providing a picture of an activity of the microorganisms over a time span on the nutrient medium as an analyte in the liquid transport medium is fed into the nutrient medium in the space in the chamber through the membrane from each of the reservoirs;

(b) supplying the molecule to the semi-solid nutrient medium containing the microorganisms with the molecule from the transport medium over the span of time; and (c) recording the growth of the microorganisms in the space over time using the recorder means.

21. The method of claim 20 wherein the recording is with a camera which is activated periodically during the recording.

22. The method of claim 21 wherein the illuminating means is activated intermittently during the recording in conjunction with the taking of a picture with the camera.

23. The method of claim 20 wherein multiple compounds are provided in the chamber by the transport medium.

24. The method of claim 23 wherein one of the multiple compounds is in each of the reservoirs.

25. The method of claim 24 wherein bacteria as the microorganism are introduced into the space in the chamber.

26. The method of claim 20 wherein a gas supply means is used for regulating an atmosphere in the chamber.

27. The method of claim 20 wherein a temperature control means is used for regulating a temperature of the chamber.

28. The method of claim 20 wherein an effluent chamber is used to collect the transport medium from the outlet of the reservoir and provide a back pressure to prevent siphoning of the transport medium from the semi-solid nutrient medium.

29. The method of claim 20 wherein tubes connect the reservoirs to the effluent means and wherein a height of the effluent means relative to the reservoirs is used to provide a back pressure in the reservoirs to maintain the diffusion gradient.

30. The method of claim 29 wherein the effluent means is an effluent chamber which collects the transport medium from the reservoirs and provides the back pressure by the height.

31. An apparatus which functions for recording observations of microorganisms in an environment by providing a diffusion gradient in the environment which comprises:

(a) a chamber having a space which supports a semi-solid nutrient medium for microorganism growth, wherein the chamber has spaced apart transparent walls and sidewalls defining a space between the walls;

(b) a reservoirs on the chamber for a liquid transport medium to be provided in the chamber each reservoir with an opening into the space in the chamber through an opening in the chamber, wherein the reservoirs are removably mounted on the chamber;

(c) a diffusion membrane mounted between the opening in the reservoir and the opening in the chamber at a height so that the membrane is covered by the semi-solid nutrient medium wherein the diffusion membrane allows a molecule in the transport medium through the opening in the reservoirs, the diffusion membrane and the opening in the chamber into the semi-solid nutrient medium to establish the diffusion gradient of the molecule in the chamber for the microorganism wherein one of the reservoirs can serve as a sink to receive the molecule moving from the semi-solid nutrient medium out of the diffusion gradient;

(d) an inlet into and an outlet from the reservoirs for flow of the liquid transport medium;

(e) a supply means for supplying the liquid transport medium to the inlet to the reservoirs; and (f) an effluent means for receiving the transport medium from the outlet of the reservoirs without destroying the diffusion gradient of the molecule in the semi-solid nutrient medium, wherein tubes connect the reservoirs to the effluent means and wherein a height of the effluent means relative to the reservoirs provides a back pressure through the tubes in the reservoirs to maintain the diffusion gradient.

32. The apparatus of claim 31 wherein the effluent means is an effluent chamber which collects the transport medium from the reservoirs and provides the back pressure.

33. A method for the detection of microorganism growth in an environment by providing a diffusion gradient in the environment which comprises:

(a) providing an apparatus which is a system which comprises: a chamber having a space which supports a semi-solid nutrient medium for the growth of the microorganisms, wherein the chamber has spaced apart transparent walls and sidewalls defining a space between the walls; at least one reservoir mounted on the chamber for a liquid transport medium to be provided in the chamber each reservoir with an opening into the space in the chamber through an opening in the chamber, wherein the reservoirs are removably mounted on the chamber; a diffusion membrane mounted between the opening in the reservoirs and the opening in the chamber at a height so that the membrane is covered by the semi-solid nutrient medium wherein the diffusion membrane allows a molecule in the transport medium through the opening in the reservoirs, the diffusion membrane and the opening in the chamber into the semi-solid nutrient medium to establish the diffusion gradient of the molecule in the chamber for the microorganism wherein one of the reservoirs serves as a sink to receive the molecule moving from the semi-solid nutrient medium out of the diffusion gradient; an inlet into and an outlet from the reservoirs for flow of the liquid transport medium; a supply means for supplying the liquid transport medium to the inlet to the reservoirs; an effluent means for receiving the transport medium from the outlet of the reservoirs without destroying the diffusion gradient of the molecule in the semi-solid nutrient medium, wherein tubes connect the reservoirs to the effluent means and wherein a height of the effluent means relative to the reservoirs provides a back pressure through the tubes in the reservoirs to maintain diffusion gradient;

(b) adjusting the height of the effluent means to provide the diffusion gradient and growing the microorganisms in the semi-solid nutrient medium in the presence of the diffusion gradient of the molecule; and (c) recording the growth of the microorganisms in the space over time using the recorder means.

34. The method of claim 33 wherein the effluent means is an effluent chamber which collects the transport medium from the reservoirs and provides the back pressure by adjusting the height.

* * * * *

UNITED STATES PATENT AND TRADEMARK OFFICE
CERTIFICATE OF CORRECTION

PATENT NO. : 5,589,352

DATED : December 31, 1996

INVENTOR(S) : John A. Breznak, David Emerson and John K. Koh

It is certified that error appears in the above-indentified patent and that said Letters Patent is hereby corrected as shown below:

Column 2, line 10, "HS" should be --$HS^-$--.

Column 3, line 21, "FIG 1" should be --FIG 1A--.

Column 3, line 44, "day p3" should be --day 3--.

Column 4, line 50, "reservoir 4" should be --reservoir 24--.

Column 5, line 57, "bottom plate 2B" should be --bottom plate 12B--.

Column 7, line 28, "1.5 min" should be --1.5 mm--.

Column 10, line 56, "N" and "r" should be --$N_s$-- and --$r_s$--, respectively.

Column 11, line 12, "$K_z(S_r-S_i)$" should be -- $K_s(S_r-S_i)$ --.

Column 16, line 34, " 1 x 10-4M" should be --$1 \times 10^{-4}M$--.

UNITED STATES PATENT AND TRADEMARK OFFICE
CERTIFICATE OF CORRECTION

PATENT NO. : 5,589,352
DATED : December 31, 1996
INVENTOR(S) : John A. Breznak, David Emerson and John K. Koh It is certified that error appears in the above-indentified patent and that said Letters Patent is hereby corrected as shown below:

Column 18, line 37 (Claim 1), "reservoir" should be --reservoirs--.

Column 19, line 39 (Claim 17), "reservoir" should be --reservoirs--.

Column 21, line 1 (Claim 31), "a reservoirs on the" should be --at least one reservoir on the--.

Column 21, line 7 (Claim 31), "the reservoir" should be --the reservoirs--.

Signed and Sealed this

Twenty-seventh Day of May, 1997

Attest:

BRUCE LEHMAN

Attesting Officer

Commissioner of Patents and Trademarks